(12) United States Patent
Prasad et al.

(10) Patent No.: US 9,775,822 B2
(45) Date of Patent: Oct. 3, 2017

(54) CHLOROGENIC ACID COMPOSITION

(71) Applicants: Kodimule Shyam Prasad, Bangalore (IN); Harakanahalli Lingaraju Basavegowda, Bangalore (IN)

(72) Inventors: Kodimule Shyam Prasad, Bangalore (IN); Harakanahalli Lingaraju Basavegowda, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 0 days.

(21) Appl. No.: 14/814,494

(22) Filed: Jul. 30, 2015

(65) Prior Publication Data

US 2016/0081967 A1 Mar. 24, 2016

Related U.S. Application Data

(60) Provisional application No. 62/031,135, filed on Jul. 30, 2014.

(51) Int. Cl.
*A61K 31/235* (2006.01)
*A61K 31/216* (2006.01)
*A61K 36/74* (2006.01)

(52) U.S. Cl.
CPC ............ *A61K 31/216* (2013.01); *A61K 36/74* (2013.01); *A61K 2236/00* (2013.01)

(58) Field of Classification Search
CPC .................................................... A61K 31/216
USPC .......................................................... 514/533
See application file for complete search history.

(56) References Cited

PUBLICATIONS

Farah (in Coffee: Emerging Health Effects and Disease Prevention, First Edition. Edited by Yi-Fang Chu., 2012 John Wiley & Sons, Inc. Published 2012 by Blackwell Publishing Ltd).*
Murase et al. Am J Physiol Endocrinol Metab 300: E122-E133, 2011.*
Venkatesh et al., J. Pharm. Sci. 89, 145-54 (2000).*
Monteiro The Journal of Nutrition, Journal of Nutrition (2007), 137(10), 2196-2201.*

* cited by examiner

*Primary Examiner* — Nizal Chandrakumar
(74) *Attorney, Agent, or Firm* — Office of Timothy M. Brown

(57) ABSTRACT

The present invention is directed compositions derived from green coffee bean extract and methods for the use and manufacture of such compositions. The compositions of the invention have unique ratios of chlorogenic acids which offer a therapeutic effect in the treatment of a variety of conditions and disorders. Methods for using the compositions of the invention include, but not limited to, methods for treating obesity and methods for regulating serum lipids.

3 Claims, 13 Drawing Sheets

CHLOROGENIC ACID COMPOSITION

CROSS-REFERENCE TO RELATED APPLICATIONS

This application claims priority under 35 U.S.C. §119(e) to provisional application Ser. No. 62/031,135 filed Jul. 30, 2014, the contents of which are incorporated herein by reference in their entirety for all purposes.

FIELD OF THE INVENTION

The invention generally relates to compositions of chlorogenic acids and methods for their manufacture and use in managing obesity. More particularly, such compositions relate to formulations of chlorogenic acids from green coffee extract.

BACKGROUND

Obesity is a condition manifesting almost directly as a consequence of modern day's lifestyle that encompasses sedentary work-culture, high fat, calorie-rich diet, dearth of regular exercise or physical activity, addiction to habit forming substances such as tobacco and alcohol and high day-to-day stress levels. Obesity has reached epidemic proportions globally, with more than 1 billion adults overweight—at least 300 million of them clinically obese—and is a major contributor to the global burden of chronic disease and disability. Ischemic heart disease or cardiovascular diseases are the conditions, often referred to as lifestyle diseases, have obesity as one of their root causes. Ischemic heart disease is the number one cause of death in the world today, according to a recent World Health Organization (WHO) report that may be found at http://who.int/mediacentre/factsheets/fs310/en/. Cardiovascular diseases (CVDs) have killed nearly 17 million people in the year 2011 which amounts to 3 in every 10 deaths. CVDs are among the top causes of death, in India as well, as per the WHO. The importance of managing obesity is, thus, evident.

Often coexisting in developing countries with undernutrition, obesity is a complex condition, with serious social and psychological dimensions, affecting virtually all ages and socioeconomic groups. Obesity and overweight pose a major risk for other serious chronic diseases, including type 2 diabetes, hypertension, and stroke and certain forms of cancer. The health consequences range from increased risk of premature death, to serious chronic conditions that reduce the overall quality of life.

It is, therefore, safe to state that managing obesity would substantially aid in reducing the global mortality, increasing the life expectancy and increasing the quality of life. Dietary changes, exercise and activity, behavioral change, prescription weight-loss medications and weight-loss surgery are the common treatment arms for managing obesity. The treatment method to be undertaken often depends on the preferred choice of an individual undergoing treatment as well as the level of obesity.

The preferred treatment modality for weight loss is dieting and physical exercise. However, due to busy schedules and sedentary lifestyles, following-up with the first two methods seems to be practiced in an irregular manner. Weight loss surgery, on the other hand, is ruled out by a host of the population due to high costs involved. Therefore, there is a gradual shift towards an increase in the use of drugs.

The drugs used for weight-loss, generally alter one of the fundamental processes of the human body such as weight regulation by altering appetite, metabolism or absorption of calories. Orlistat is the only anti-obesity medication which is currently approved by the FDA for long term use. It reduces the intestinal fat absorption by inhibiting the pancreatic enzyme lipase. Rimonabant and Sibutramine are the other drugs that had initially been approved for the treatment of obesity, but were banned eventually due to safety concerns. Because of the potential side effects, it is recommended that anti-obesity drugs only be prescribed for obesity where it is hoped that the benefits of the treatment outweigh its risk.

What is needed in the art therefore is a nutrition-based intervention that provides an inexpensive alternative to aid weight loss and weight management. The inventors of the present invention, therefore, envisage a cost-effective and safe herbal composition or a dietary supplement which is used for the management of obesity.

SUMMARY OF THE INVENTION

Some of the objects of the present disclosure are described herein below:

It is an object of the present disclosure to provide a composition for the management of obesity.

It is another object of the present disclosure to provide a composition for the management of obesity, which is cost-effective and non-toxic.

It is yet another object of the present disclosure to provide a composition of CGA-7 isomers from Indian Green coffee bean extract for reducing body weight, removal of abdominal fat tissue, removal BAT, reducing cholesterol levels, improving HDL levels and restoring glucose levels.

It is still another object of the present disclosure to provide a process for the preparation of CGA-7 Complex.

It is yet another object of the present disclosure to provide a method for the treatment and/or prevention of diseases associated with obesity, amongst others.

Other objects and advantages of the present disclosure will be more apparent from the following description which is not intended to limit the scope of the present disclosure.

DETAILED DESCRIPTION

Figure 1A:
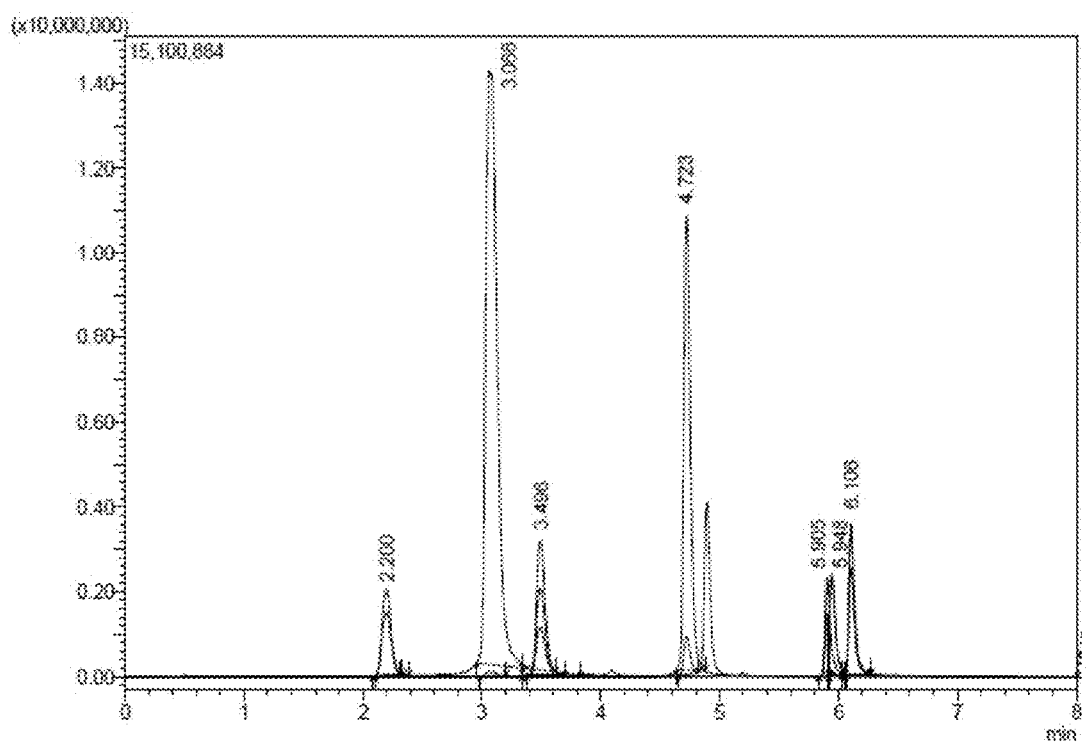
FIGS. 1A-C show an MS chromatogram of a composition of the invention.
Figure 1B:
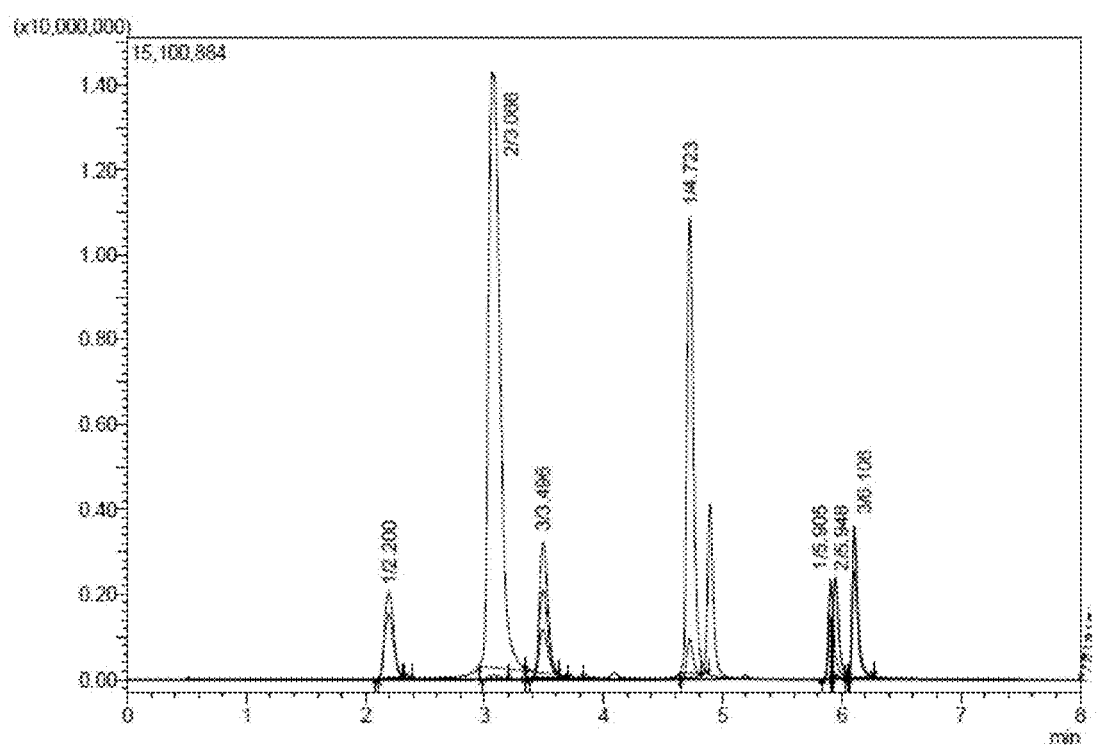
Figure 1C:
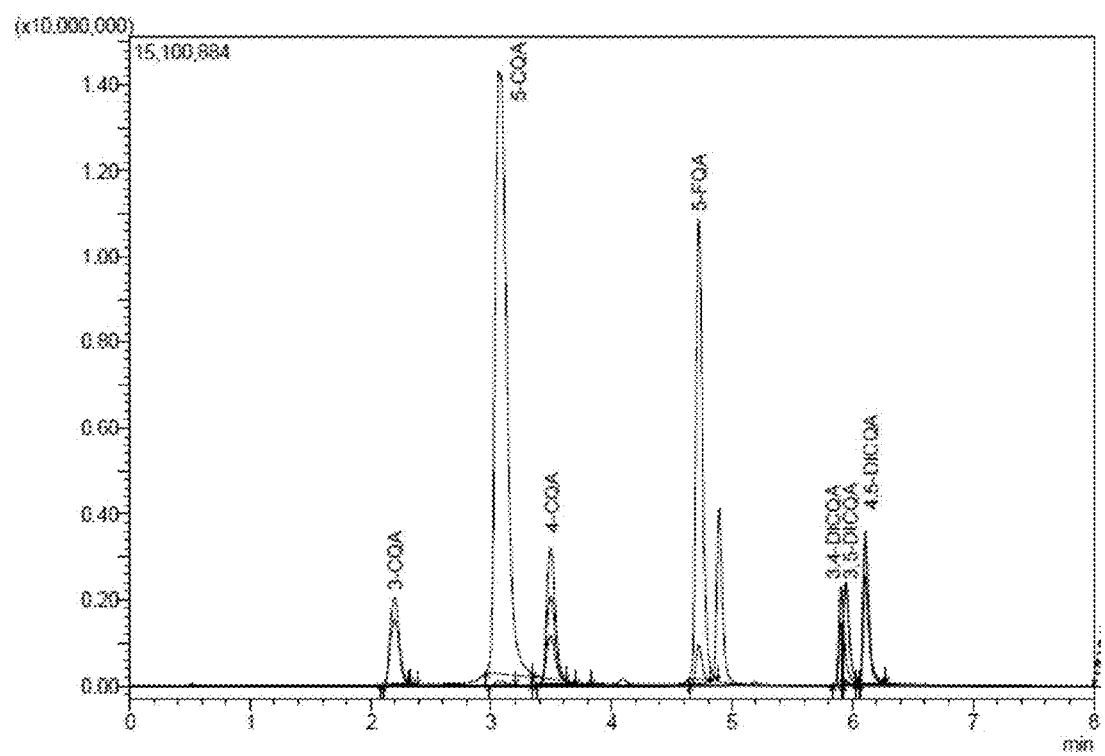
Figure 2:
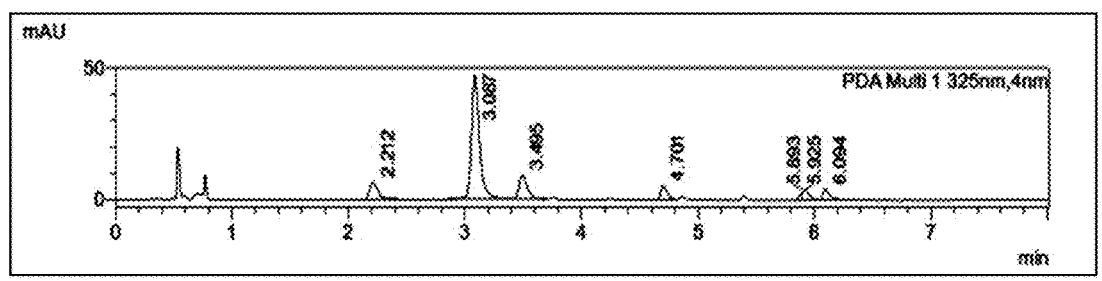
FIG. 2 shows an LS chromatogram of a composition of the invention.

In accordance with one aspect of the present disclosure, there is provided a process for the preparation and use of a composition comprising one or more chlorogenic acids (e.g. a CGA-7 complex). The part plants used for the preparation of the composition of the invention may be fresh and/or dried. Typically, the composition is prepared by obtaining an extract of one or more chlorogenic acids. Such extract can be obtained by processes including, but not limited to, alcoholic, hydro-alcoholic and aqueous extract. Further, the composition is prepared by using techniques selected from the group that includes but is not limited to hot stirring, Soxhlet extraction, percolation, decoction, maceration and supercritical fluid extraction. The solvent used for extraction can be a polar organic solvent and/or a non-polar organic solvent. Solvents suitable for use with the invention include, but are not limited to water, methanol, ethanol, butanol, hexane, acetone, chloroform, petroleum ether and acetonitrile. In one embodiment of the present disclosure, green coffee beans are subjected to extraction to obtain a combination of one or more chlorogenic acids.

The composition may be formulated to attain a particular chlorogenic acid content. The composition may have a total chlorogenic acid content of between about 20-60% w/w. The composition may have a total chlorogenic acid content, by weight, of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, as well as any amount intervening these specifically described amounts. The total chlorogenic acid content may be 42.50±2.5 w/w %. The total chlorogenic acid content may be constituted from one or more of 3 CQA, 5 CQA, 4 CQA, 3,4 Di CQA, 3,5 Di CQA, 4,5 Di CQA. The total chlorogenic acid content may contain, for example, a chlorogenic acid content of about 1-15% w/w 3 CQA, about 5-50% w/w 5 CQA, about 1-20% w/w 4 CQA, about 0.5-10% w/w 3,4 Di CQA, about 0.5-10% w/w 3,5 Di CQA, about 0.5-10% w/w 4,5 Di CQA, or combination thereof. The composition may contain 4.1±1.42 w/w % 3CQA, 28±4.65 w/w % 5 CQA, 6.5±2.25 w/w % 4 CQA, 0.84±0.26 w/w % 3,4 Di CQA, 1.23±0.34 w/w % 3,5 Di CQA, and 1.85±0.42 w/w % 4,5 Di CQA.

In one embodiment of the present invention, the composition comprises a combination of chlorogenic acids. In one non-limiting embodiment, the composition comprises 3-caffeoylquinic acid (3-CQA), 5-caffeoylquinic acid (5-CQA), 4-caffeoylquinic acid (4-CQA), 5-feruloylquinic acids (5-FQA), 3,4 dicaffeoylquinic acids (3,4 di CQA), 3,5 dicaffeoylquinic acids (3,5 di CQA), and 4,5 dicaffeoylquinic acids (4,5 di CQA).

In one non-limiting embodiment, the composition comprises 3-caffeoylquinic acid (3-CQA) at about 7.23%, 5-caffeoylquinic acid (5-CQA) at about 25.43%, 4-caffeoylquinic acid (4-CQA) at about 9.51%, 5-feruloylquinic acids (5-FQA) at about 1.84%, 3,4 dicaffeoylquinic acids (3,4 di CQA) at about 2.79%, 3,5 dicaffeoylquinic acids (3,5 di CQA) at about 1.90%, and 4,5 dicaffeoylquinic acids (4,5 di CQA) at about 3.74%.

The term "about" as used herein refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%, or any intervening range thereof.

In accordance with another aspect of the present disclosure, there is provided a process for the preparation of a dosage form comprising the composition of the invention. In accordance with yet another aspect of the present disclosure there is provided a complex mixture for managing obesity that comprises a combination of chlorogenic acids. The phyto-constituents included in the composition of the present disclosure can be in any form that permits an effective dosage for use such as the management of obesity. Suitable forms for administering the composition include, but are not limited to, extracts, granules, powders, semisolids, isolated fractions, oils, solutions, suspensions, emulsions and semisolids. In one embodiment, the composition is a complex mixture obtained from Indian Green coffee bean.

The composition of the present invention may be administered by various routes including but not limiting to topical, oral, buccal, sub-lingual, parenteral, rectal, and inhalation. The composition may be in the form of a dosage form that includes but is not limited to powders, pills, tablets, pellets, capsules, thin films, solutions, sprays, syrups, linctuses, lozenges, pastilles, chewing gums, pastes, vaporizers, suspensions, emulsions, ointments, creams, lotions, liniments, gels, drops, topical patches, buccal patches, injections and the like. Typically, the composition further comprises at least one pharmaceutically acceptable excipient.

The composition of the present invention can be used in any application in which administration of the composition to a subject provides beneficial health effects. Suitable applications for administration of the composition include, but are not limited to, preventing oxidation (antioxidant activity), controlling and/or reducing body weight, controlling and/or reducing body mass index, controlling and/or reducing obesity, management of hyperlipidemic conditions, reducing oxidative stress, maintaining a healthy lipid profile, regulating blood glucose levels, treatment of liver cirrhosis, treatment of atherosclerosis, and treatment bacterial infection. The composition of the invention may be administered to reduce low density lipids. The composition of the invention may be administered to increase high density lipids. The composition of the invention may be administered to reduce low density lipids and increase high density lipids. Significantly, the composition is non-toxic and non-mutagenic. In some aspects of the The phrase "body mass index" as used herein refers to a ratio of height to body weight that is calculated as follows:

$$BMI = \frac{mass_{kg}}{height_m^2} = \frac{mass_{lb}}{height_{in}^2} \times 703$$

The terms "obese" and "obesity" as used herein refer to a subject having a body mass index of 30 or higher.

The term "overweight" as used herein refers to a subject having a body mass index of 25 to 29.9.

The term "healthy weight" as used herein refers to a subject having a body mass index of 18.5 to 24.9.

The phrase "treating obesity" as used herein refers to reducing BMI in an obese subject, reducing body fat in an obese subject, or reducing body weight in a subject.

As used herein, the term "controlling" refers to maintaining the state of a condition so as to prevent an increase or decrease in the condition or an increase or decrease in the symptoms of the condition. Controlling may refer to controlling obesity wherein the state of obesity of a subject is maintained such that the body weight or body mass index of a subject is maintained at a level without any appreciable increase in body weight or body mass index.

As used herein, the term "reduce," "reducing" and the like refer to any measurable decrease in a condition or parameter that results from the administration of the composition of the invention to a subject when compared to the absence of the administration of the composition, such as compared to the administration of a control composition (e.g. a placebo). In some aspects of the invention, administration of a composition of the invention to a subject reduces obesity or body weight in the subject when compared to the administration of a control substance to a subject. In some aspects of the invention, administering the compositions of the invention maintains body weight (i.e. prevents an increase in body weight or an increase in percent body fat).

As used herein, the terms "treatment," "treating," and the like, when used in reference to a subject, refer to obtaining a desired pharmacologic and/or physiologic effect, including without limitation achieving a reversal, improvement or elimination of the symptoms of a disease or condition. The effect can be prophylactic in terms of completely or partially preventing a disease or symptom thereof and/or can be therapeutic in terms of achieving an improvement or elimination of symptoms, or providing a partial or complete cure for a disease and/or adverse affect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; (c) relieving the disease, e.g., causing regression of the disease, e.g., to completely or partially eliminate symptoms of the disease; and (d) restoring the individual to a pre-disease state, e.g., reconstituting the hematopoietic system.

The compositions of the invention can be administered to treat obesity in a subject. The compositions of the invention can be administered to reduce body mass index in an obese subject. The compositions of the invention can be administered to reduce body mass index in an overweight subject. The compositions of the invention may be administered to control or prevent weight gain in a subject. In some aspects of the invention may be administered to maintain or achieve a healthy weight in a subject. The compositions of the invention can be administered to reduce body fat in an obese subject. The compositions of the invention can be administered to reduce body fat in an overweight subject. The compositions of the invention may be administered to control or prevent body fat gain in an obese subject. The compositions of the invention may be administered to control or prevent body fat gain in an overweight subject. The compositions of the invention may be administered to control or prevent body fat gain in a healthy weigh subject.

As used herein, "administer" or "administration" refers to the act of physically delivering a substance as it exists outside the body into a subject. Administration includes all forms known in the art for delivering therapeutic agents, including but not limited to oral, topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal). The compositions described herein can be administered intravenously.

The compositions of the invention may be administered in an effective amount. The phrase an "effective amount" as used herein refers to an amount of a composition of the invention that is sufficient to achieve the effect for which the composition is administered (e.g., to maintain or reduce obesity).

The terms "subject," "patient," "subject in need thereof," and "patient in need thereof" are herein used interchangeably and refer to mammal, including humans. Subjects may also be cattle, sheep, goats, pigs or other animals used in animal husbandry. In a preferred embodiment the subject is a human. The subject can be a human suffering from obesity or having an unhealthy body weight.

The composition of the invention may be obtained from any source material capable of providing the chlorogenic acids disclosed herein. The compositions of the invention can be obtained from green coffee bean material. In one non-limiting embodiment of the invention, the composition is derived from Indian green coffee bean material. The term "green coffee bean" as used herein refers to unroasted mature or immature coffee beans. Green coffee beans can be processed by wet or dry methods for removing the outer pulp and mucilage, and can have an intact wax layer on the outer surface. When immature coffee beans are immature, they are green. When mature, they have a brown to yellow or reddish color, and typically weigh 300 to 330 mg per dried coffee bean. The compositions of the invention may comprise green coffee extract as an extract of unroasted, green coffee beans. The compositions of the invention may be obtained from the green coffee bean. The compositions of the invention may be obtained from the outer pulp (mucilage) of the bean. The compositions of the invention may be obtained from the green coffee bean. The compositions of the invention may be obtained from a combination of the green coffee bean and the pulp of the coffee bean.

The present disclosure is further described in the light of the following non-limiting examples which are set forth for illustration purpose only and not to be construed for limiting the scope of the present invention.

Example 1: Process for Preparation of the Complex Mixture of the Present Disclosure (CGA-7 Complex)

100 kg of Green coffee bean was stacked in a vertical 1.0 KL extractor. The bottom of the extractor comprised of a perforated plate on which filtration cloth was fixed. About six bed volumes of 70% v/v ethyl alcohol was added. Extraction was continued at 75-78° C. about 7-8 hrs with continuous circulation of extract with transfer pump. After completion of extraction, filter the extract through 5 micron SS candle filter and clear extract was collected in a cleaned receiver tank. The bed was re-extracted by adding 4 bed volumes of 70% ethyl alcohol 3 more times and temperature was maintained at 75-78° C. about 7-8 hrs. All the extracts were collected in a receiver tank and combined extract was concentrated in a reactor under vacuum at 80±5° C. till extract was free from ethyl alcohol. Solution was made up to the TDS to 20-25 w/v % with de-ionized water.

The above extract solution was passed through 500 Liter of XAD-4 resin and the extract was loaded through the resin at the rate of 2-3 bed volumes/hour. The resin was washed with 2-3 bed volumes of de-ionized water at the rate of 2-3 bed volumes/hour. The extract was eluted with 2-3 bed volumes of 70 v/v % Ethyl alcohol at the rate of 2-3 bed volumes/hour. The eluent was concentrated in a reactor at 80±5° C. till free from alcohol. The solution TDS was made up to 25-30 w/v % and spray dried at 215±5° C. to obtain the complex mixture of CGA-7.

The composition of the chlorogenic acid isomers was determined by the HPLC method and the following results were obtained:

TABLE 1

Peak Table showing Types of Chrologenic acids

| Peak | Name | Ret. Time | Area | Area % | Height | Height % |
|---|---|---|---|---|---|---|
| 1 | 3 CQA | 3.209 | 1904533 | 12.529 | 395880 | 13.745 |
| 2 | 5 CQA | 5.017 | 7126683 | 46.883 | 1394953 | 48.431 |
| 3 | 4 CQA | 5.218 | 2612578 | 17.187 | 521622 | 18.110 |
| 4 | 5 FQA | 7.489 | 703664 | 4.629 | 136587 | 4.742 |
| 5 | 3,4 Di CQA | 11.049 | 941037 | 6.191 | 162285 | 5.634 |
| 6 | 3,5 Di CQA | 11.549 | 694548 | 4.569 | 111103 | 3.857 |
| 7 | 4,5 Di CQA | 12.659 | 1218027 | 8.013 | 157843 | 5.480 |
| Total | | | 15201070 | 100 | 2880273 | 100 |

The fingerprint of the composition of the chlorogenic acid isomers was determined by the LC-MS/MS method and the results that were obtained are depicted in FIGS. 1A-C and FIG. 2.

Example 2: In-Vitro Studies of the Complex Mixture (CGA-7 Complex) of the Present Disclosure Antioxidant Assay:
DPPH Scavenging Assay The free radical scavenging capacity of CGA-7 Complex was determined using DPPH scavenging assay (Sarojini et al., 2011). DPPH solution was prepared in 95% methanol. Freshly prepared DPPH solution was taken in test tubes and coffee preparations were added and incubated for 20 min. The absorbance was read at 515 nm using a spectrophotometer. Blank was prepared containing the same volume of reaction mixture without any tested samples. The percentage of scavenging was calculated using formula % Scavenging=$Ac-As/Ac \times 100$ Where AC was the absorbance of the control (blank without extract) and As was the absorbance in the presence of the extract Metal Chelating Activity The chelating of ferrous ions by the Plant extracts was estimated by the following method. CGA-7 Complex was added to a solution of 2 mM $FeCl_2$ (0.05 ml), the reaction was initiated by the addition of 5 mM ferrozine (0.2 ml). Then the mixture was shaken vigorously and kept for 10 min at room temperature [26]. Absorbance of the solution was measured at 562 nm. The percentage of inhibition of ferrozine-$Fe^{2+}$ complex formation was calculated.

Chelating rate (%)=$Ac-As/Ac \times 100$

Where AC was the absorbance of the control (blank without extract) and As was the absorbance in the presence of the extract Superoxide Anion Scavenging Activity Superoxide anion scavenging activity of CGA-7 Complex was measured according to the method of (Nishimiki et al., 1972). Prepare all the solutions in this experiment using phosphate buffer (pH 7.4). Add 1 ml of NBT (156 μM), 1 ml of NADH (468 μM) and 3 ml of test samples. to all test tubes. The reaction is started by adding 100 ml of PMS (60 μM) and incubate the mixture at 25° C. for 5 min followed by measurement of absorbance at 560 nm. The percentage of scavenging was calculated using formula % Scavenging=$Ac-As/Ac \times 100$ Where AC was the absorbance of the control (blank without extract) and As was the absorbance in the presence of the extract Reducing Power Assay The reductive ability of CGA-7 Complex was determined. The test samples were mixed with 2.5 ml of 0.2 M phosphate buffer (pH 6.6) and 2.5 ml of 1% potassium ferricyanide [$K_3Fe(CN)_6$]. Reaction mixture was incubated at 50° C. for 20 min, add 2.5 ml of 10% trichloroacetic acid, then centrifuge (650 rpm at room temperature) for 10 min. The upper layer solution (2.5 ml) was mixed with 2.5 ml of distilled water and 0.5 ml of 0.1% $FeCl_3$. Absorbance was measured at 700 nm. Higher the absorbance at 700 nm indicates higher reducing power ability (Oyaizu, 1986).

Total Antioxidant Activity

The phosphomolybdenum method is based on the reduction of Mo (VI) to Mo (V) by the antioxidant compound and the formation of a green phosphate/Mo (V) complex with a maximal absorption at 695 nm. The antioxidant activity of the test sample will be determined by the phosphomolybdenum method as described by Prieto et al., (1999). Briefly, 0.3 ml of test sample combined with 3 ml of reagent solution (0.6M sulfuric acid, 28 mM sodium phosphate and 4 mM ammonium molybdate). The reaction mixture will be incubated at 95° C. for 90 min and cooled to room temperature.

Measure the absorbance of the solution at 695 nm against blank. The total antioxidant capacity expressed as the number of equivalents of ascorbic acid (AAE).
Results:
Sample Name: CGA-7 Complex

TABLE 2

| In-vitro assays of CGA-7 Complex | | | | | | | | |
|---|---|---|---|---|---|---|---|---|
| DPPH scavenging assay | | | Superoxide scavenging assay | | | Metal chelating | | |
| Conc in µg/ml | Absorbance @ 517 nm | % inhibition | Conc in µg/ml | Absorbance @ 560 nm | % inhibition | Conc in µg/ml | Absorbance @ 562 nm | % inhibition |
| Blank | 1.801 | | Blank | 0.337 | | Blank | 0.702 | |
| 100 µg | 0.886 | 50.81 | 100 µg | 0.110 | 67.36 | 100 µg | 0.726 | −3.42 |
| | 1.007 | 44.09 | | 0.102 | 69.73 | | 0.739 | −5.27 |
| | 0.985 | 45.31 | | 0.120 | 64.39 | | 0.746 | −6.27 |
| | 0.967 | 46.31 | | 0.123 | 63.50 | | 0.734 | −4.56 |
| | 0.976 | 45.81 | | | 66.25 | | | −4.88 |
| | | 45.97 | | | | | | |

| Total antioxidant assay | | | Reducing power assay | | |
|---|---|---|---|---|---|
| Conc in µg/ml | Absorbance @ 695 nm | AAE (µg) | Conc in µg/ml | Absorbance @ 700 nm | AAE (µg) |
| 100 µg | 0.078 | 14.78 | 100 µg | 0.545 | 58.55 |
| | 0.078 | 14.80 | | 0.590 | 63.37 |
| | 0.080 | 14.95 | | 0.598 | 64.16 |
| | 0.074 | 14.50 | | 0.560 | 60.09 |
| | 0.078 | 14.80 | | 0.555 | 59.63 |
| | | 14.76 | | | 61.16 |

Example 3: In-Vivo Studies of CGA-7 Complex of the Present Disclosure

A] Acute Oral Toxicity Study in Rats with CGA-7 Complex

Single-dose oral toxicity of the CGA-7 Complex was evaluated in albino Wistar rats. A limit test was performed in which female rats received a single oral administration of the CGA-7 Complex at a dose of 2000 mg/kg body weight. Following dosing, the limit test rats were observed daily and weighed weekly. A gross necropsy examination was performed on all limit test animals at the time of scheduled euthanasia (day 14). No mortality occurred during the duration of the limit test. Further, no significant gross internal findings were observed at necropsy on study day 14.

Under the experimental conditions described, the acute oral $LD_{50}$ of CGA-7 complex was estimated to be greater than 2000 mg/kg in the rat.

B] Repeated Dose 90 Days Toxicity with CGA-7 Complex

Repeated dose 90 day oral toxicity study was performed with CGA-7 complex in both male and female Wistar rats followed by 14 day recovery period. To determine target organ toxicity, No observed adverse effect level (NOAEL) and reversibility of signs of toxicity after recovery period.

Results of acute oral toxicity studies in Wistar albino rats indicated the acute oral $LD_{50}$ of CGA-7 complex was estimated to be greater than 2000 mg/kg in the rats. Based on the above results; three doses were selected as 250, 500 and 1000 mg/kg b.w. Oral route of administration was selected because it is the proposed therapeutic route.

Observations

Clinical signs of toxicity: No clinical signs of toxicity were observed in all male and female groups of animals throughout the dosing period of 90 days and during the recovery period of 14 days.

Mortality: All the male and female groups of animals were survived throughout the dosing period of 90 days and during the recovery period of 14 days.

Body Weight: Body weights were recorded 0 to 90 days for all groups and continued for day 97 and 104 for reversal groups.

Body weight gain: A significant decrease in body weight gain was seen in all groups of animals treated with CGA-7 Complex at 250, 500 and 1000 mg/kg b.w. in both males and females when compared with control. During the reversal period the animals also showed a significant decrease in body weight gain to normal when compared with control reversal group.

Food Intake: No effect of treatment in all groups of animals was noted on food consumption throughout the dosing period of 90 days and during the recovery period of 14 days.

Functional observations: The functional observational parameters performed showed no changes in all groups of male and female animals.

Blood Analysis

Hematology: No significant changes were observed in all groups of male and female animals when compared with those of respective control groups. No dose dependent changes were seen.

Clinical Chemistry: No significant changes were observed in all groups of males and females when compared with those of respective control groups.

Urine analysis: No changes were noted in Urine analysis of all groups of male and female animals when compared with those of respective control groups.

Sacrifice and Pathology

Relative Organ weight: No significant changes were observed in all groups of male and female animals when compared with those of respective control groups. No dose dependent changes were observed.

Gross pathology: No gross changes were observed in all groups of male and female animals.

Histopathological studies: No changes were seen in brain, liver, heart, spleen, kidneys, ovaries, large intestine and adrenal glands in animals treated with CGA-7 Complex 1000 mg/kg b.w. when compared with control.

Conclusion: Based on the above findings, the no observed adverse effect level (NOAEL) of CGA-7 complex was found to be 1000 mg/kg·b.w. for both female and male Wistar rats when given orally for 90 days followed by 14 day recovery period.

C] Anti-Obesity Activity of the CGA-7 Complex:

Objective: The objective was to investigate the effect of the CGA-7 complex against high fat diet fed rats.

Procedure:

Model: High fat diet in rats
Composition of High Fat Diet
25% Lard
5% Soyabean oil
5% starch
65% Normal commercial available rat feed Male Wistar rats were divided into six groups with six animals in each group.

TABLE 3

Specifications of groups

| S. NO | Group | Test substance |
|---|---|---|
| 1 | Group I | Normal feed + Vehicle (distilled water) |
| 2 | Group II | High fat diet + Vehicle (distilled water) |
| 3 | Group III | High fat diet + Standard drug (orlistat 30 mg/kg) |
| 4 | Group IV | High fat diet + CGA 7 Complex (50 mg/kg) |
| 5 | Group V | High fat diet + CGA 7 Complex (100 mg/kg) |
| 6 | Group VI | High fat diet + CGA 7 Complex (150 mg/kg) |

Parameters Evaluated

Body weight was measured once every 2 days. Food intake was measured daily for 42 days.

On day 43, all the animals were kept overnight fasting before sacrifice. Blood was collected by puncturing the retro orbital plexus. Serum was separated by centrifugation at 3000 rpm for 10 minutes.

Serum was estimated for glucose, cholesterol, triglycerides and HDL. LDL and atherogenic index were also calculated. Liver, mesenteric, brown adipose tissue (BAT), left and right perirenal fat pads, left and right epididymal pads were isolated and weighed. Liver was isolated and estimated for liver triglycerides and cholesterol levels.

Statistical Analysis

Data were expressed as mean±SEM & analyzed by one way ANOVA followed by Dunnett's t test using graph pad prism version 5. Differences were considered significant at a p value of <0.05.

Results

TABLE 4

Effect of CGA 7 Complex on body weight in male rats

| Groups | Final weight | Initial weight | Difference in body weight |
|---|---|---|---|
| Group I | 220.5 ± 2.54 | 150.1 ± 2.67 | 68.41 ± 1.18 |
| Group II | 230.3 ± 5.57 | 137.0 ± 0.32 | 112.0 ± 4.51*** $^a$ |
| Group III | 218.4 ± 2.65 | 130.3 ± 0.56 | 88.01 ± 3.68*** $^b$ |
| Group IV | 211.7 ± 2.42 | 136.1 ± 0.62 | 75.65 ± 3.44*** $^b$ |
| Group V | 229.7 ± 1.94 | 163.8 ± 2.33 | 65.88 ± 2.14*** $^b$ |
| Group VI | 199.0 ± 2.08 | 138.4 ± 1.07 | 60.63 ± 2.89*** $^b$ |

Values are expressed in terms of SEM ± Mean. Data were analyzed by one way ANOVA followed by Dunnett's t test. Number of animals in each group n = 6.
$^a$ Comparison made with control group.
$^b$ Comparison made with high fat diet group.
***$P < 0.001$.

TABLE 5

Effect of CGA 7 Complex on average food intake in male rats

| Groups | Average food intake g/rat |
|---|---|
| Group I | 14.93 ± 0.77 |
| Group II | 8.26 ± 0.51***$^a$ |
| Group III | 8.54 ± 0.40$^{nsb}$ |
| Group IV | 7.78 ± 0.45$^{nsb}$ |
| Group V | 8.96 ± 0.45$^{nsb}$ |
| Group VI | 6.98 ± 0.35$^{nsb}$ |

Values are expressed in terms of SEM ± Mean. Data were analyzed by one way ANOVA followed by Dunnett's t test. Number of animals in each group n = 6.
$^a$Comparison made with control group.
$^b$Comparison made with high fat diet group.
***$P < 0.001$
$^{ns}$non significant.

TABLE 6

Effect of CGA 7 Complex on liver organ weight, mesenteric, brown adipose tissue (BAT), perirenal fat pads and epididymal fat pad.

| Groups | Liver | Mesenteric fat | BAT | Peri renal fat pad tissue Right | Peri renal fat pad tissue Left | Epididymal fat pad Right | Epididymal fat pad Left |
|---|---|---|---|---|---|---|---|
| Group I | 3.87 ± 0.18 | 0.59 ± 0.06 | 0.06 ± 0.004 | 0.30 ± 0.02 | 0.28 ± 0.01 | 0.35 ± 0.03 | 0.38 ± 0.01 |
| Group II | 4.50 ± 0.19*$^a$ | 1.31 ± 0.12***$^a$ | 0.24 ± 0.01***$^a$ | 1.22 ± 0.12***$^a$ | 0.85 ± 0.05***$^a$ | 0.58 ± 0.04***$^a$ | 0.60 ± 0.02***$^a$ |
| Group III | 3.47 ± 0.11***$^b$ | 0.98 ± 0.03*$^b$ | 0.19 ± 0.01**$^b$ | 0.65 ± 0.04*$^b$ | 0.61 ± 0.05*$^b$ | 0.48 ± 0.01*$^b$ | 0.50 ± 0.01*$^b$ |
| Group IV | 3.56 ± 0.10***$^b$ | 1.01 ± 0.07*$^b$ | 0.20 ± 0.01*$^b$ | 0.52 ± 0.03***$^b$ | 0.54 ± 0.03***$^b$ | 0.44 ± 0.02**$^b$ | 0.46 ± 0.03***$^b$ |
| Group V | 3.57 ± 0.12***$^b$ | 1.0 ± 0.04*$^b$ | 0.17 ± 0.01***$^b$ | 0.43 ± 0.02***$^b$ | 0.41 ± 0.03***$^b$ | 0.41 ± 0.02***$^b$ | 0.38 ± 0.02***$^b$ |
| Group VI | 3.39 ± 0.10***$^b$ | 1.0 ± 0.07*$^b$ | 0.17 ± 0.01***$^b$ | 0.36 ± 0.02***$^b$ | 0.38 ± 0.03*$^b$ | 0.40 ± 0.03***$^b$ | 0.37 ± 0.01***$^b$ |

Data were analyzed by one way ANOVA followed by Dunnett's t test. Number of animals in each group n = 6.
$^a$Comparison made with control group.
$^b$Comparison made with high fat diet group.
***$P < 0.001$
**$P < 0.01$
*$P < 0.05$.

TABLE 7

Effect of CGA 7 Complex on serum glucose, total cholesterol, triglyceride, HDL-c and LDL-c levels (mg/dL)

| Groups | Glucose | Total cholesterol | Triglyceride | HDL-c | LDL-c |
|---|---|---|---|---|---|
| Group I | 84.53 ± 4.62 | 56.00 ± 1.44 | 70.56 ± 3.59 | 24.56 ± 0.88 | 17.33 ± 1.78 |
| Group II | 131.00 ± 5.88***$^a$ | 78.08 ± 1.40***$^a$ | 137.7 ± 7.95***$^a$ | 16.73 ± 0.59***$^a$ | 33.81 ± 2.11***$^a$ |
| Group III | 109.7 ± 3.93**$^b$ | 63.38 ± 0.95***$^b$ | 77.63 ± 4.27***$^b$ | 20.47 ± 1.08*$^b$ | 27.39 ± 1.07$^{nsb}$ |
| Group IV | 89.29 ± 2.79***$^b$ | 62.23 ± 1.74***$^b$ | 86.32 ± 5.06***$^b$ | 20.22 ± 0.82*$^b$ | 25.12 ± 2.33*$^b$ |
| Group V | 87.63 ± 3.28***$^b$ | 58.16 ± 2.18***$^b$ | 75.36 ± 4.17***$^b$ | 20.50 ± 1.10*$^b$ | 22.59 ± 2.67**$^b$ |
| Group VI | 86.23 ± 3.50***$^b$ | 45.20 ± 2.37***$^b$ | 62.98 ± 2.97***$^b$ | 20.51 ± 0.94*$^b$ | 12.09 ± 2.31***$^b$ |

Data were analyzed by one way ANOVA followed by Dunnett's t test. Number of animals in each group n = 6.
$^a$Comparison made with control group.
$^b$Comparison made with high fat diet group.
***P < 0.001
**P < 0.01
*P < 0.05

TABLE 8

Effect of CGA 7 Complex on atherogenic index

| Group | Atherogenic Index |
|---|---|
| Group I | 1.30 ± 0.10 |
| Group II | 3.72 ± 0.22***$^a$ |
| Group III | 2.20 ± 0.20***$^b$ |
| Group IV | 2.18 ± 0.15***$^b$ |
| Group V | 1.91 ± 0.23***$^b$ |
| Group VI | 1.22 ± 0.14***$^b$ |

Data were analyzed by one way ANOVA followed by Dunnett's t test. Number of animals in each group n = 6.
$^a$Comparison made with control group.
$^b$Comparison made with high fat diet group.
***P < 0.001

TABLE 9

Effect of CGA 7 Complex on liver cholesterol & triglyceride levels

| Group | liver cholesterol | liver triglycerides |
|---|---|---|
| Group I | 23.92 ± 1.50 | 50.51 ± 2.16 |
| Group II | 69.53 ± 2.54***$^a$ | 87.93 ± 3.56***$^a$ |
| Group III | 49.66 ± 3.28***$^b$ | 64.64 ± 3.44***$^b$ |
| Group IV | 48.48 ± 3.58***$^b$ | 57.68 ± 4.25***$^b$ |
| Group V | 44.61 ± 4.45***$^b$ | 59.91 ± 2.73***$^b$ |
| Group VI | 28.53 ± 2.69***$^b$ | 36.04 ± 4.42***$^b$ |

Data were analyzed by one way ANOVA followed by Dunnett's t test. Number of animals in each group n = 6.
$^a$Comparison made with control group.
$^b$Comparison made with high fat diet group.
***P < 0.001
**P < 0.01
* P < 0.05

Conclusion

The CGA 7 complex reduces body weight, removes abdominal fat tissue, removes brown adipose tissue, reduces cholesterol levels, improves HDL c levels, and restores glucose levels.

Example 4: Clinical Evaluation of CGA-7 Complex of the Present Disclosure

A Prospective, Randomized, Double Blind, Placebo Controlled Clinical Trial to Evaluate Efficacy and Safety of CGA-7 Complex in Reducing the Bodyweight in Obese Patients.

The subjects had to complete 5 visits including 1 screening visit and 4 scheduled visits; i.e., screening visit, Visit 1 (baseline)—Day 1, Visit 2—Day 14±3, Visit 3—Day 28±3, Visit 4—Day 56±3. The screening visit consisted of patient consent form, multiple laboratory tests, physical examinations, anthropometric measurements and understands inclusion/exclusion criteria. After screening, subjects were randomized and assigned to Group A and Group B for CGA-7 Complex and placebo treatment respectively. Primary outcomes reduction in body weight and BMI on visit 2, visit 3 and visit 4 were recorded. Baseline quality of life assessment (SF-36) was also carried out. During visit 2 & 3 the anthropometric measurements, physical examination, adverse events, and concomitant medications if any were recorded. In final visit, physical examinations, anthropometric measurements, lipid profile, fasting blood glucose, HbA1c, quality of life assessment, adverse events, concomitant medications were recorded. The unused tablets were collected back.

The effect of CGA-7 Complex was validated in the absence of exercise, walking and without diet restrictions during the course of the trial.

Sample Size

Total 42 patients were screened and among them 30 were included in the study as per inclusion criteria. Subjects were randomized and equal no of subjects were assigned in CGA-7 Complex treatment group A and placebo treatment group B. Two patients were dropped out from both groups without any information during study.

Statistical Analysis

Paired t-test was used to measure the change from the baseline. ANOVA was used in order to observe the changes in the various parameters after the follow up visits scheduled, followed by appropriate post-hoc test.

Results

Body Weight

Figure 3:
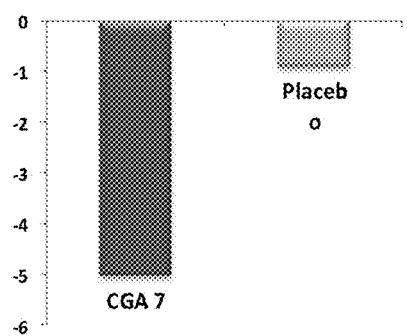
FIG. 3 shows the percent reduction of body mass index resulting from the administration of a composition of the invention.

As shown in FIG. 3, in the CGA-7 Complex treated group, baseline mean body weight was 80.6±10 which was reduced up to 76.57±10.2 on 56$^{th}$ day. Where as in placebo treated group, on 56$^{th}$ day weight reduction was negligible compare to baseline mean body weight.

There was 5% reduction in body weight observed in CGA-7 Complex treated group compared to baseline, which is significant compared to placebo treated group. In placebo treated group only 0.9% of reduction was seen in body weight compared to baseline.

BMI

Figure 4:
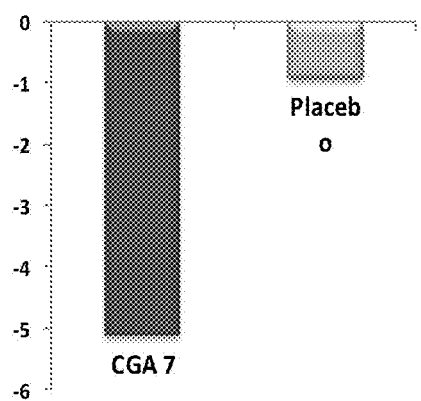
FIG. 4 shows the percent reduction of body mass index resulting from the administration of a composition of the invention.

As shown in FIG. 4, mean BMI of the CGA-7 Complex treated group at baseline was 30.53±0.62 which was significantly reduced to 28.97±0.73 on last visit. The same was found to be slightly decrease in placebo treated subjects.

CGA-7 Complex treated group has shown 5.10% reduction in BMI on $56^{th}$ day where as it was only 0.9% in placebo treated group.

Waist Circumference

Figure 5:
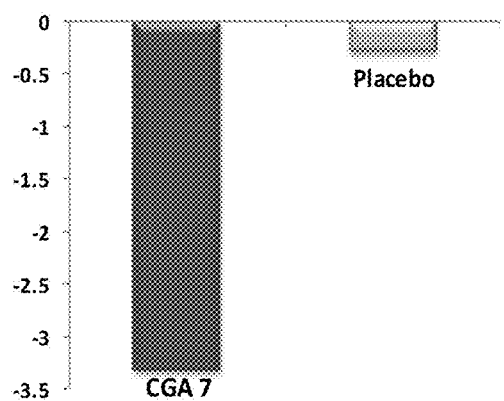
FIG. 5 shows the percent reduction of waist circumference resulting from the administration of a composition of the invention.

As shown in FIG. 5, there was a significant reduction in waist circumference on $56^{th}$ day in CGA-7 Complex treated group compared to baseline which was 103.28±4.14 and 99.85±5.36, respectively. Whereas, placebo treated group had shown negligible improvement in waist circumference.

Hip Circumference

Figure 6:
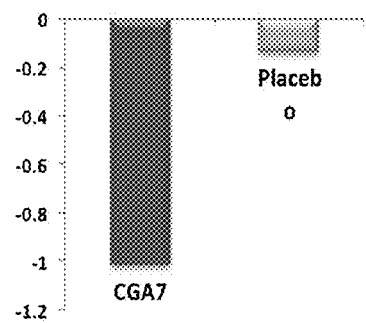
FIG. 6 shows the percent reduction of hip circumference resulting from the administration of a composition of the invention.

As shown in FIG. 6, hip circumference was significantly improved in the CGA-7 Complex treated group compared to placebo treated group. The baseline mean hip circumference was 105.85±4.88 which was reduced to 104.78±4.88 after 56 days treatment with CGA-7 Complex. 1.01% of reduction has been seen in CGA-7 Complex treated group. Which was only 0.13% in Placebo treated group.

Lipid Profile

Figure 7:
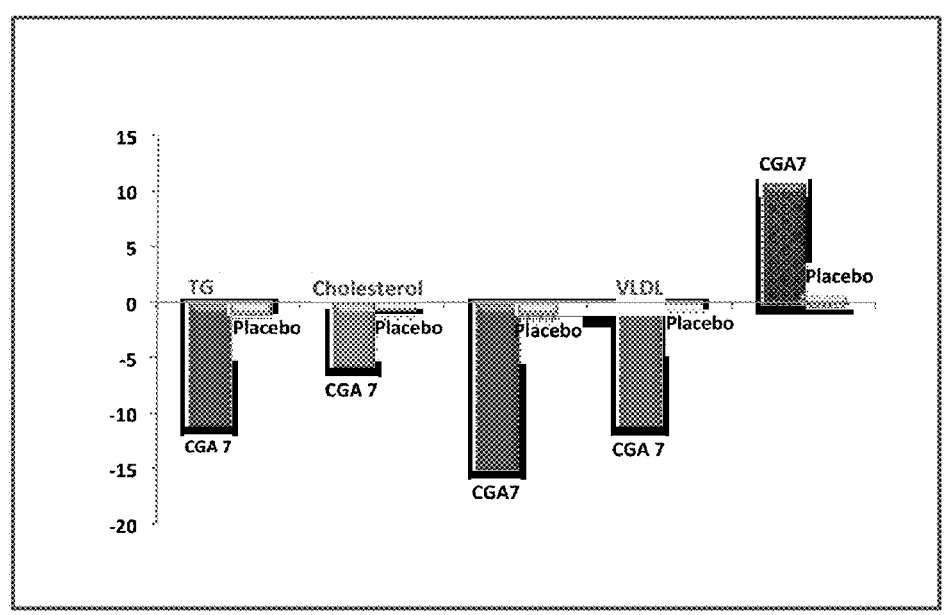
FIG. 7 shows the effect of a composition of the invention on lipid profile.
Figure 8A:
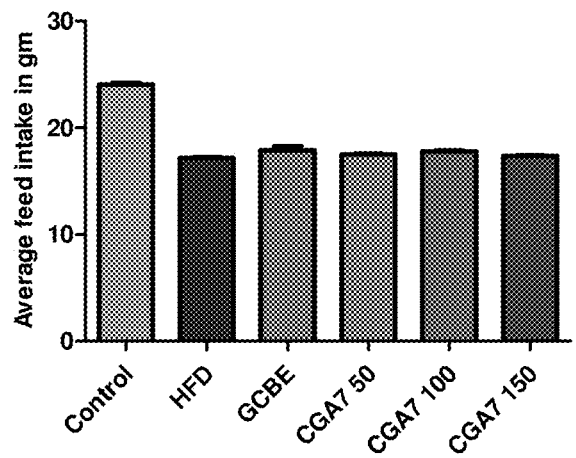
FIGS. 8A and 8B show that weight gain and average feed intake pattern where CGA7 complex at 100 and 150 mg/kg show decrease in weight gain compared to HFD and GCBE groups which is statistically significant. There is no difference in feed intake in between HFD and other treated group.
Figure 8B:
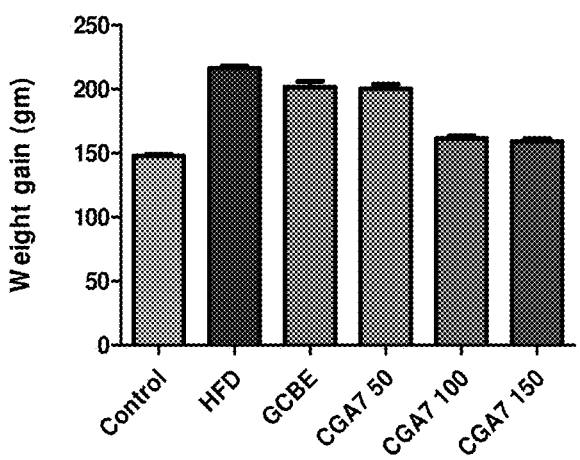
Figure 9A:
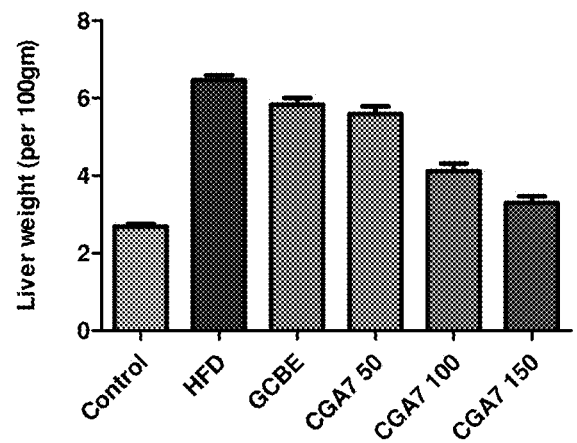
FIGS. 9A-9E represent changes in liver and adipose tissues weight. CGA7 complex at 100 and 150 mg·kg dose inhibits fat deposition in liver, BAT, mesenteric fat, epididymal and perirenal fat compared to HFD and GCBE groups which is statistically significant.
Figure 9B:
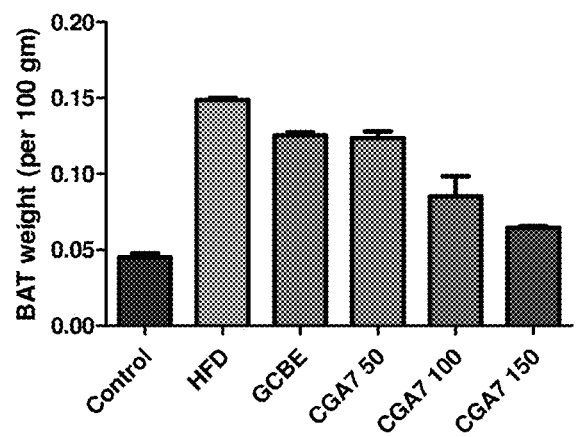
Figure 9C:
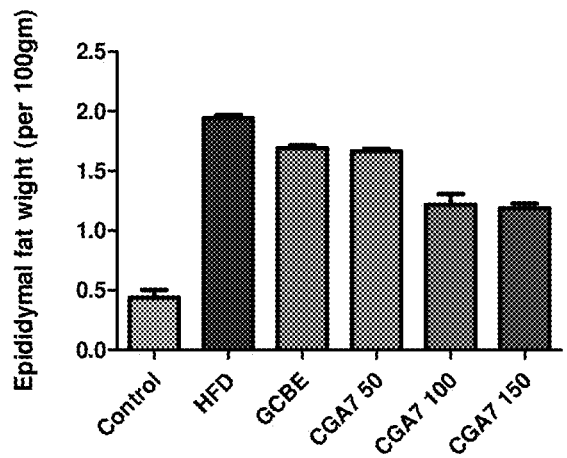
Figure 9D:
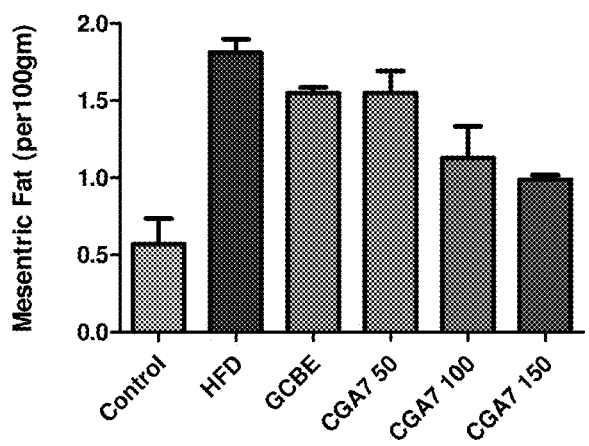
Figure 9E:
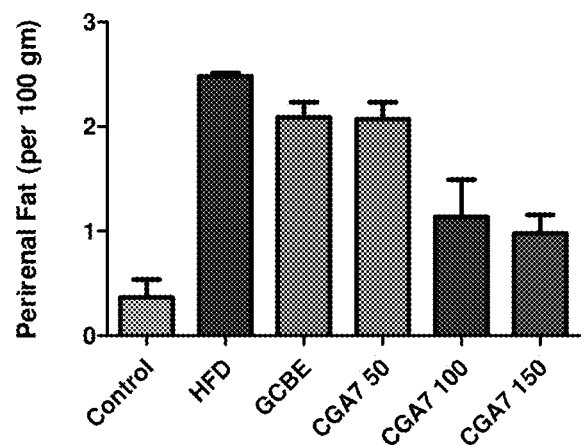
Figure 10A:
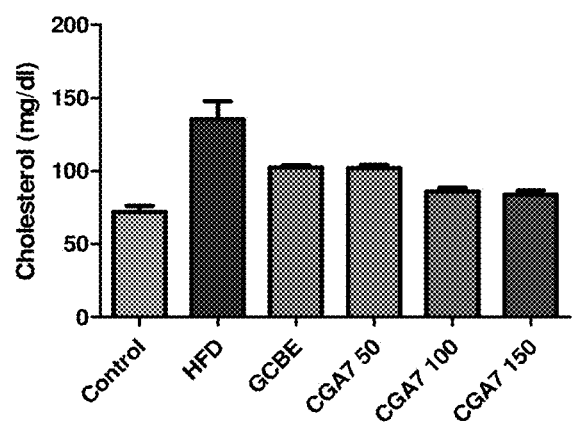
FIGS. 10A-10D show changes in cholesterol, TG, glucose and HDL blood serum level. CGA7 complex 100 and 150 mg·kg groups have decreased cholesterol, TG and glucose compared to HFD and GCBE groups which is statistically significant. CGA7 complex treated groups have significantly improved HDL level.
Figure 10B:
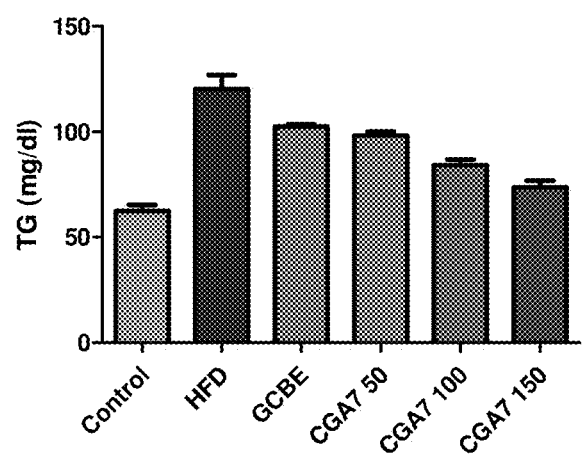
Figure 10C:
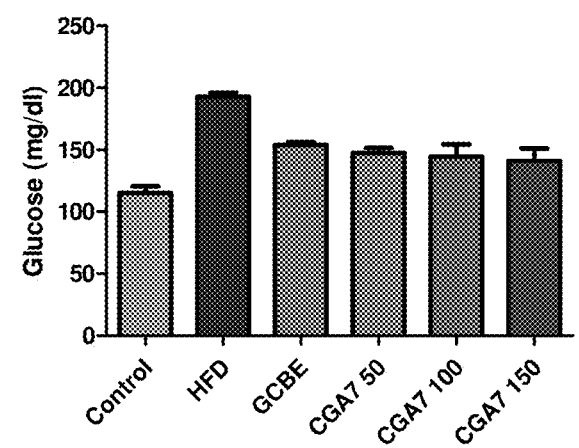
Figure 10D:
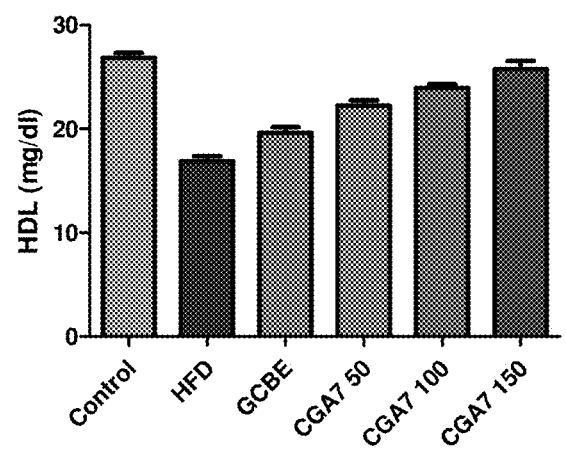
Figure 11:
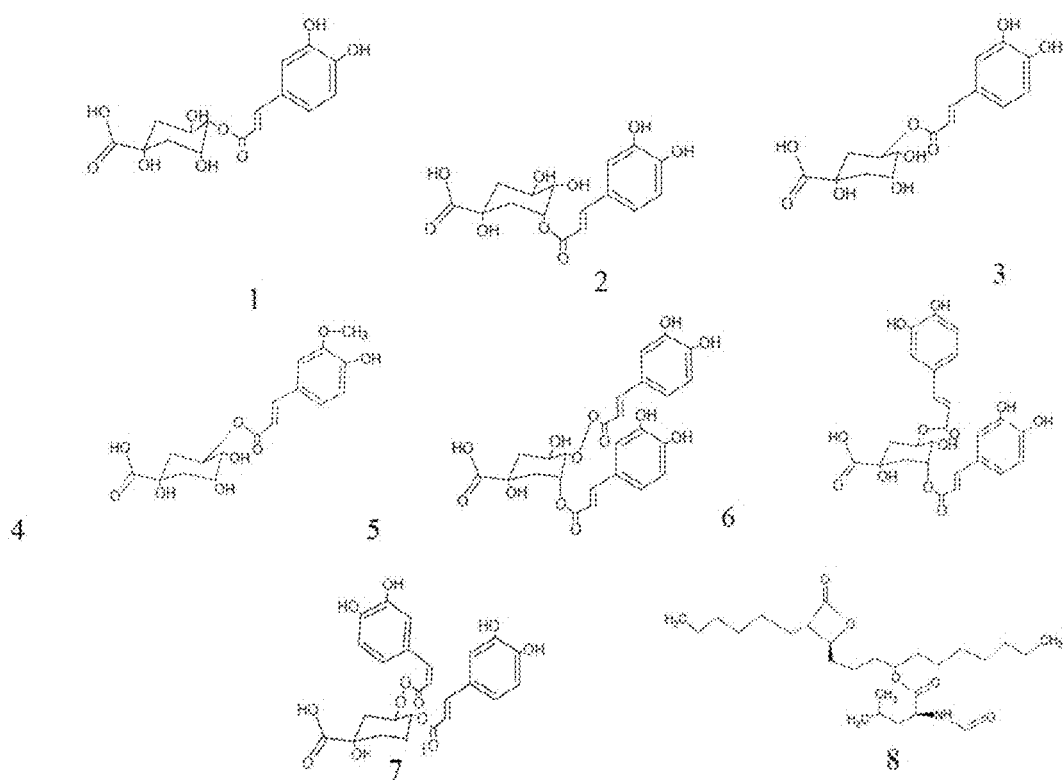
FIG. 11 shows the structure of ligand molecules: (1) 3-O-Caffeoylquinic acid; (2) 4-O-Caffeoylquinic acid; (3) 5-O-Caffeoylquinic acid; (4) 5-O-Feruloylquinic acid; (5) 3,4-O-Dicaffeoylquinic acid; (6) 3,5-O-Dicaffeoylquinic acid; (7) 4,5-O-Dicaffeoylquinic acid; and (8) Orlistat.

As shown in FIG. 7, the results collected have shown that CGA 7 Complex has significant improvement in lipid profile. The mean triglyceride level at baseline was 151±39.39 which decreased significantly to 134.43±38.15 at Day 56 after treatment with CGA 7 Complex and the percentage of triglyceride levels reduced compared to baseline is 10.97%.

The mean total cholesterol values at baseline 172.07±32.99 which decreased to 162.36±32.10 at the Day 56 after treatment with CGA 7 Complex and the Percentage of Total cholesterol levels reduced compared from baseline to visit 4 is 5.64%.

The mean HDL level at baseline was 37.91±8.29 which increased significantly to 42±7.75 at Day 56 after treatment with CGA 7 Complex and the Percentage of HDL level increased is 10.78%.

The mean LDL level at baseline was 103.96±27.18 which decreased significantly to 88.5±29.62 at Day 56 after treatment with CGA 7 Complex and the Percentage of LDL levels reduced compared from baseline to visit 4 is 14.87%

The mean VLDL level at baseline was 30.2±7.87 which decreased significantly to 26.88±7.63 at Day 56 after treatment with CGA 7 Complex and the Percentage of VLDL levels reduced compared from baseline to visit 4 is 10.99%.

The results collected have shown that Placebo has less improvement in lipid profile. Triglyceride level has been slightly decreased compared from baseline to visit 4. The baseline triglyceride value was 150.71±45.96 decreased to 149.71±45.86 at Day 56 after treatment with Placebo and the Percentage of Triglyceride level reduced compared from baseline to visit 4 is 0.7%.

The total cholesterol level has been slightly decreased compared from baseline to visit 4. The baseline total cholesterol value was 174.21±32.03 decreased to 173.57±31.95 at the Day 56 after treatment with Placebo and the Percentage of total cholesterol level reduced compared from baseline to visit 4 is 0.4%.

The mean HDL level has shown no change compared from baseline to visit 4. The baseline HDL value was 36.14±7.26 and 36.79±6.92 at Day 56 after treatment with Placebo.

The mean LDL slightly decreased compared from baseline to visit 4. The baseline LDL value was 107.93±27.03 decreased to 106.84±26.88 at Day 56 after treatment with Placebo. The Percentage of LDL level reduced compared from baseline to visit 4 is 1.0%.

The mean VLDL level has been slightly decreased compared from baseline to visit 4. The baseline VLDL value was 28.13±11.79 decreased to 29.94±9.17 after treatment with Placebo and the Percentage of total VLDL level reduced compared from baseline to visit 4 is 6.3%.

CGA 7 Complex is statistically significant in reducing triglycerides, cholesterol, LDL and VLDL than Placebo.

CGA 7 Complex was statistically significant in increasing HDL than placebo. Overall, CGA 7 Complex exhibited significant reduction in triglycerides, cholesterol and LDL levels and significant increase in HDL levels.

TABLE 10

Effect of CGA7 Complex on body weight, BMI, Waist and hip circumference, serum triglycerides, cholesterol, LDL and VLDL

| S. N. | Parameters | Visit 1 | Visit 4 | Difference | % decrease |
|---|---|---|---|---|---|
| 1 | Body weight(kg) | 80.6 ± 10 | 76.57 ± 10.2 | 4.03 | 5.00 |
| 2 | Body mass index(BMI kg/m$^2$) | 30.53 ± 0.62 | 28.97 ± 0.73 | 1.56 | 5.10 |
| 3 | Waist circumference(cm) | 103.28 ± 4.14 | 99.85 ± 5.36 | 3.43 | 3.32 |
| 4 | Hip circumference(cm) | 105.85 ± 4.88 | 104.78 ± 4.88 | 1.07 | 1.01 |
| 5 | Triglycerides(mg/dL) | 151 ± 39.39 | 134.43 ± 38.15 | 16.57 | 10.97 |
| 6 | Cholestrol(mg/dL) | 172.07 ± 32.99 | 162.36 ± 32.10 | 9.71 | 5.64 |
| 7 | LDL(mg/dL) | 103.96 ± 27.18 | 88.5 ± 29.62 | 15.46 | 14.87 |
| 8 | VLDL(mg/dL) | 30.2 ± 7.87 | 26.88 ± 7.63 | 3.32 | 10.99 |

Values are expressed in terms of Mean ± SD

TABLE 11

Effect of CGA7 Complex on serum HDL

| S N. | Parameters | Visit 1 | Visit 4 | Difference | % increase |
|---|---|---|---|---|---|
| 1 | HDL(mg/dL) | 37.91 ± 8.29 | 42 ± 7.75 | 4.09 | 10.78 |

Values are expressed in terms of Mean ± SD

TABLE 12

Effect of PLACEBO on body weight, BMI, Waist and hip circumference, serum triglycerides, cholesterol, LDL and VLDL

| S. N. | Parameters | Visit 1 | Visit 4 | Difference | % decrease |
|---|---|---|---|---|---|
| 1 | Body weight(kg) | 74.03 ± 9.7 | 73.39 ± 9.4 | 0.64 | 0.864 |
| 2 | Body mass index(BMI kg/m$^2$) | 31.01 ± 1.10 | 30.73 ± 1.18 | 0.29 | 0.90 |
| 3 | Waist circumference(cm) | 100.85 ± 5.89 | 100.57 ± 4.81 | 0.28 | 0.27 |
| 4 | Hip circumference(cm) | 104.92 ± 7.19 | 104.78 ± 5.02 | 0.14 | 0.13 |
| 5 | Triglycerides(mg/dL) | 150.71 ± 45.96 | 149.71 ± 45.86 | 1 | 0.7 |
| 6 | Cholestrol(mg/dL) | 174.21 ± 32.03 | 173.57 ± 31.95 | 0.64 | 0.4 |
| 7 | LDL(mg/dL) | 107.93 ± 27.03 | 106.84 ± 26.88 | 1.1 | 1.01 |
| 8 | VLDL(mg/dL) | 28.13 ± 11.79 | 29.94 ± 9.17 | 1.81 | 6.4 |

Values are expressed in terms of Mean ± SD

TABLE 13

Effect of PLACEBO on serum HDL

| S.N. | Parameters | Visit 1 | Visit 4 | Difference | % increase |
|---|---|---|---|---|---|
| 1 | HDL(mg/dL) | 36.14 ± 7.26 | 36.79 ± 6.92 | 0.65 | 1.7 |

Values are expressed in terms of Mean ± SD

Conclusion: CGA7 complex is effective in reducing body weight, reduces BMI, hip and waist circumferences, improves lipid profile by increasing HDL serum level and decreasing triglycerides, cholesterol and LDL serum levels, and is safe with no unwanted effects.

Example 5: CGA7 Complex is Superior to Coffee Bean Extract in the Management of Obesity, Serum Cholesterol, Triglyceride, HDL and Glucose Levels Obesity is a disarray of energy balance and primarily considered as a disorder of lipid metabolism. Obesity and the comorbidities associated with obesity remain a global health problem. It is one of the major public health problems in the world because of its association with an increased risk of various chronic diseases, including cardiovascular diseases, type 2 diabetes, hypertension, dyslipidemia and cancers. Recent estimates in the USA indicate that approximately one-third of the adult population is obese. World Health Organization (WHO) assigns obesity as global epidemic. Globally, approximately 1.6 billion adults are overweight and at least 400 million adults are obese. Further WHO projects that by 2015 approximately 2.3 billion people will be overweight and more than 700 million will be obese.

Coffee is widely used as beverages all over the world. It has numerous health benefits against obesity, metabolic disorders like type 2 diabetes. The main active constituent of coffee is chlorogenic acids with different isomers present in it. Chlorogenic acid is highly antioxidant and provides protection against liver cirrhosis, atherosclerosis, bacterial infection, obesity. CGA-7 complex contains more than 52% of seven different isomers of chlorogenic acid, extracted from the green coffee bean. Several in vitro and in vivo study support that chlorogenic acid has antiobesity activity.

With respect to this, CGA-7 complex containing more than 52% of chlorogenic acid (Proprietary extract of *Coffea arabica* from VIDYA HERBS PVT LTD) was evaluated against high fat fed S.D. male rats in comparison with green coffee bean extract.

Objective

To investigate the role of CGA-7 Complex proprietary herbal extract of *Coffea arabica* from VIDYA HERBS against high fat diet fed S.D. male rats with compared to green coffee bean extract (GCBE).

Materials and Methods

Material: CGA 7 Complex

Model: High fat diet (HFD) in S.D rats

Composition of high fat diet: –200 g of fat/kg (170 g of lard oil+30 g of corn oil) and 1% cholesterol.

TABLE 14

Grouping of animals

| Group | Treatment | Dose (mg/kg, orally) |
|---|---|---|
| I | Control + Vehicle | Distilled water 10 ml/kg |
| II | HFD + Vehicle | Distilled water 10 ml/kg |
| III | HFD + GCBE | 100 mg/kg |
| IV | HFD + CGA-7 | 50 mg/kg |
| V | HFD + CGA-7 | 100 mg/kg |
| VI | HFD + CGA-7 | 150 mg/kg |

36 male S.D rats were divided in 6 groups each containing six. Normal rat chow diet was fed to group-1 for 42 days. HFD was fed to group 2-6 for 42 days. Respective treatment was given to all groups for 42 days as described in table.

Parameters Evaluated:

Body weight was measured once every 2 days. Food intake was measured daily for 42 days.

On day 43, all the animals were kept overnight fasting before sacrifice. Blood was collected by puncturing the retro orbital plexus. Serum was separated by centrifugation at 3000 rpm for 10 minutes.

Serum was estimated for glucose, cholesterol, triglycerides and HDL.

Liver, mesenteric, brown adipose tissue (BAT), left and right perirenal fat pads, left and right epididymal pads were isolated and weighed.

Statistical Analysis: Data were expressed as mean±SEM & analyzed by one way ANOVA followed by Dunnett's t test using graph pad prism version 5. Differences were considered significant at a p value of <0.05.

Results

Values are expressed in terms of SEM±Mean. Data were analyzed by one way ANOVA followed by Dunnett's t test. Number of animals in each group n=6. [a]Comparison made with control group. [b]Comparison made with high fat diet group. *$P<0.001$, $P<0.01$

TABLE 15

Effect of CGA 7 COMPLEX on body weight in male rats

| | | | |
|---|---|---|---|
| Control + Vehicle | 293.8 ± 1.23 | 145.9 ± 0.79 | 147.9 ± 1.09 |
| HFD + Vehicle | 360.0 ± 1.21 | 143.6 ± 0.62 | 216.3 ± 1.61***[a] |
| HFD + GCBE (100 mg/kg) | 345.7 ± 5.06 | 144.1 ± 0.61 | 201.7 ± 4.49**[b] |
| HFD + CGA-7(50 mg/kg) | 346.5 ± 3.22 | 146.1 ± 0.50 | 200.3 ± 3.51**[b] |
| HFD + CGA-7(100 mg/kg) | 311.3 ± 2.27 | 144.1 ± 0.99 | 167.2 ± 3.02***[b] |
| HFD + CGA-7(150 mg/kg) | 304.2 ± 1.81 | 145.1 ± 1.08 | 159.1 ± 2.30***[b] |

TABLE 16

Effect of CGA 7 COMPLEX on average feed intake

| Group | Treatment | Feed intake (g/per rat) |
|---|---|---|
| I | Control + Vehicle | 24.05 ± 0.13 |
| II | HFD + Vehicle | 17.15 ± 0.08***[a] |
| III | HFD + GCBE (100 mg/kg) | 17.88 ± 0.35* [b] |
| IV | HFD + CGA-7(50 mg/kg) | 17.48 ± 0.08 |
| V | HFD + CGA-7(100 mg/kg) | 17.75 ± 0.10 |
| VI | HFD + CGA-7(150 mg/kg) | 17.34 ± 0.07 |

TABLE 17

Effect of CGA 7 COMPLEX on liver organ weight, mesenteric, brown adipose tissue (BAT), perirenal fat pads and epididymal fat pad

| Group | Treatment | Liver (per 100 g) | BAT (per 100 g) | Mesentric fat (per 100 g) | Epididymal Fat (per 100 g) | Perirenal Fat (per 100 g) |
|---|---|---|---|---|---|---|
| I | Control + Vehicle | 2.688 ± 0.07 | 0.04 ± 0.002 | 0.57 ± 0.07 | 0.44 ± 0.06 | 0.36 ± 0.07 |
| II | HFD + Vehicle | 6.467 ± 0.12***[a] | 0.15 ± 0.001***[a] | 1.81 ± 0.03***[a] | 1.94 ± 0.02***[a] | 2.48 ± 0.01***[a] |
| III | HFD + GCBE (100 mg/kg) | 5.832 ± 0.17* [b] | 0.12 ± 0.002* [b] | 1.55 ± 0.01** [b] | 1.69 ± 0.02** [b] | 2.09 ± 0.06** [b] |
| IV | HFD + CGA-7 (50 mg/kg) | 5.598 ± 0.19** [b] | 0.12 ± 0.004* [b] | 1.54 ± 0.06** [b] | 1.66 ± 0.02** [b] | 2.07 ± 0.07** [b] |
| V | HFD + CGA-7 (100 mg/kg) | 4.115 ± 0.19*** [b] | 0.08 ± 0.013*** [b] | 1.13 ± 0.08*** [b] | 1.21 ± 0.09*** [b] | 1.14 ± 0.14*** [b] |
| VI | HFD + CGA-7 (150 mg/kg) | 3.298 ± 0.17*** [b] | 0.06 ± 0.001*** [b] | 0.99 ± 0.01*** [b] | 1.18 ± 0.03*** [b] | 0.98 ± 0.07*** [b] |

Green coffee bean extract is well tolerated as anti-obesity and widely used for same. Chlorogenic acid is chief pharmacological active constituents of green coffee bean. There is lack of scientific evidences of role of chlorogenic acid in obesity management, lipid metabolism. CGA7 complex mainly contains more than 52% of seven isomers of chlorogenic acids. The effect of CGA7 complex has been investigated in high fat diet induced obese S.D male rats by comparing with green coffee bean extract.

This in vivo study revealed that CGA7 complex at the dose of 100 mg/kg and 150 mg/kg has shown 25.3% and 26.4% reduction in body weight gain respectively which are statistically significant compared to GCBE treated group (6.7%). CGA7 complex treated groups have also lowered brown adipose and white adipose tissue weight extensively compared to GCBE treated group.

Visceral adipose tissue discharges plenty of free fatty acids (FFA) and cytokines/hormones in the vein. Further these FFA transported to the liver where they interact with hepatocytes and various immune cells. It is also believed that body weight and adipose tissues weight are positively correlated with leptin and insulin levels. Cho et al studied that plasma leptin and insulin levels were high in HFD treated group which were significantly lowered by chlorogenic acid supplementation.

Due to the leptin resistance, there is increase in FFA from adipose tissue to liver. Where FFA is converted to triglycerides and causes fatty liver by increased lipogenesis, a result of hyperinsulinemia and decreased FFA oxidation. De sotillo and Hadley states that chlorogenic acid improves glucose tolerance and decreases plasma and hepatic lipids without changing triglycerides level in adipose tissue of Zucker rats at 5 mg·kg (i.v.). In this study, which is conformed where HFD group has shown increase in liver size and weight. CGA7 complex has shown significant reduction in liver and other adipose tissues weight when given orally at 100 mg/kg and 150 mg/kg compared to GCBE. CGA7 complex has reduced serum cholesterol, triglycerides and glucose levels markedly and improved HDL level compared to GCBE treated group.

Conclusion

CGA7 complex is superior to coffee bean extract in obesity management. CGA reduces 25.3% and 26.4% in body weight gain at 100 mg/kg and 150 mg/kg respectively. CGA complex also demonstrates an ability to reduce serum cholesterol, triglyceride and glucose level, and reduce fat accumulation in liver and reduce brown and white adipose tissue. CGA complex improves serum HDL levels.

Example 6: Molecular Docking Studies of CGA-7 Complex with Fat Mass and Obesity Associated Protein (LTO)

Introduction

Weight gain and obesity are major risk factors for conditions and diseases ranging from insulin resistance and type 2 diabetes mellitus to atherosclerosis and the sequelae of nonalcoholic fatty liver disease (Shoelson et al., 2007). Physiologically, obesity is a disarray of energy balance and primarily considered as a disorder of lipid metabolism (Strader et al., 1998). The condition is associated with a growing number of enzymes involved in lipid metabolic pathways. They represent a rich pool of potential therapeutic targets for obesity (Shi & Burn, 2004; Melnikova & Wages, 2006). Fat mass and obesity associated protein also known as alpha-ketoglutarate-dependent dioxygenase (FTO) is an enzyme that appears to be correlated with obesity in humans (Frayling et al., 2007). FTO contributes to the regulation of the global metabolic rate, energy expenditure and energy homeostasis. FTO contributes to the regulation of body size and body fat accumulation.

Green coffee bean extract has been reported to have potent antiobesity and hypoglyceridemic properties by in vivo studies. Chlorogenic acids are a major group of polyphenols found in raw green coffee bean and contribute significantly to the pharmacological efficacy of coffee bean extract. The objective of the present study was to explore the in silico anti-obesity activity of CGA-7 complex from green coffee bean extract by targeting FTO.

Materials and Methods

AutoDock tools was utilized to generate grids, calculate dock score and evaluate the conformers of inhibitors bound in the active site of AMPK as targets for antidiabetic activity. Automated docking is a graphical user interface. AutoDock 4.2 was employed to get docking and binding scores; which is implemented by Lamarckian genetic algorithm method. The ligand molecules i.e., the seven isomers of chlorogenic acid (FIG. 1) and Orlistat were designed and the structure was analyzed using ACD/Chemsketch. The PRODRG server was used to minimise energy of drug compounds and 3D coordinates were prepared. The protein structure file (PDB ID: 3LFM) (FIG. 2) was taken from PDB and was edited by removing the hetero atoms using Python molecule viewer. The grid map was centred at particular residues of the protein and was generated with AutoGrid. As per genetic algorithm all the torsions were allowed to rotate during docking. The Lamarckian genetic algorithm and the pseudo-Solis and Wets methods were applied for minimization, using default parameters (Rodriguez and Infante, 2011).

Results

All the seven isoforms of chlorogenic acid in CGA-7 binds very efficiently within the active pocket of FTO (FIG. 3). The result obtained is comparable to orientation of standard drug Orlistat. The binding energy required is less than that of Orlistat and the firm binding of isoforms is evident from the formation of more hydrogen bonds of ligand molecules in comparison with standard drug (Table 1).

TABLE 18

Molecular docking results of Fat mass and obesity associated protein

| Molecule | Thermodynamic parameters | | | | H-bonds | Interactions |
|---|---|---|---|---|---|---|
| | Binding energy | Ligand efficiency | | | | |
| 3-O-Caffeoylquinic acid | −8.04 | −0.32 | 1.28 | −11.32 | 5 | Leu78 His73 Arg80 Gln468 |
| 4-O-Caffeoylquinic acid | −7.01 | −0.28 | 7.21 | −10.3 | 7 | Leu78 Lys391 Asp467 Arg80 |
| 5-O-Caffeoylquinic acid | −7.43 | −0.3 | 3.56 | −10.7 | 6 | Arg80 Leu78 His73 Arg80 Gln468 |
| 5-O-Feruloylquinic acid | −5.56 | −0.21 | 84.65 | −8.84 | 5 | His73 Arg80 Gln468 Leu78 |
| 3,4-O-Dicaffeoylquinic acid | −5.32 | −0.21 | 126.75 | −8.6 | 4 | His73 Gln468 Arg80 |
| 3,5-O-Dicaffeoylquinic acid | −5.88 | −0.16 | 48.78 | −10.95 | 6 | Asp208 His73 Gln468 Lys74 Lys391 |
| 4,5-O-Dicaffeoylquinic acid | −7.73 | −0.26 | 2.14 | −12.81 | 5 | Arg80 Leu78 Lys391 His73 |
| Orlistat (Std) | −4.65 | −0.14 | 390.87 | −11.21 | 3 | Ser95 Arg80 |

Conclusion

CGA-7 as a complex mixture of 7 isoforms of chlorogenic acid from green coffee bean extract is effective in interacting with fat mass and obesity associated protein (FTO) more efficiently than the standard drug Orlistat and hence may serve as a better candidate for the development of anti-obesity drugs in future.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The disclosures of all references mentioned in this application are incorporated by reference in their entirety as if set forth verbatim herein.

REFERENCES

1. Brown J P. A review of the genetic effect of occurring flavonoids, anthraquinones and related compounds. *Mutat Res* 1980; 75(3):243-277.
2. Farnsworth N R, Akerele O, Bingel A S, Soejarto D D, Guo Z. Medicinal plants in therapy. *Bull World Health Organ.* 1985; 63(6):965-81.
3. Jovtchev G, Stergios M, Schubert I. A comparison of N-methyl-N-nitrosourea induced chromatid aberrations and micronuclei in barley meristems using FISH techniques. *Mutat Res* 2002; 517:47-51.
4. Kamboj V P. Herbal Medicine. *Curr Sc* 2000; 78(1):35-37.
5. OECD Guideline for the testing of chemicals—Repeated Dose 90-day Oral Toxicity Study in Rodents; T G 408, 21 Sep. 1998.
6. OECD Guideline No. 420, "Acute Oral Toxicity"—Fixed Dose Procedure 17 Dec. 2001.
7. Sultan A O, çelik T A. Genotoxic and antimutagenic effects of *Capparis spinosa* L. on the *Allium cepa* L. root tip meristem cells. Caryologia, 2009; 262: 114-123.
8. Song S. J., Choi S., Park T. (2014) Decaffeinated Green Coffee Bean Extract Attenuates Diet-Induced Obesity and Insulin Resistance in Mice. Evidence-Based Complementary and Alternative Medicine, 1-14.
9. Vongsak B., Sithisarn P., Gritsanapan W. (2013) Simultaneous Determination of Crypto-Chlorogenic Acid, Isoquercetin, and Astragalin Contents in *Moringa oleifera* Leaf Extracts by TLC-Densitometric Method. Evidence-Based Complementary and Alternative Medicine, 1-7.
10. Narita Y., Inouye K. (2013) Degradation Kinetics of Chlorogenic Acid at Various pH Values and Effects of Ascorbic Acid and Epigallocatechin Gallate on Its Stability under Alkaline Conditions. J. Agric. Food Chem., 61 (4), 966-972.
11. Farah A., Paulis T. D., Martin P. R., Trugo L. C. (2005) Effect of Roasting on the Formation of Chlorogenic Acid Lactones in Coffee. J. Agric. Food Chem., 53, 1505-1513.
12. Sarojini B K, Vidyagayatri M, Darshanraj C G, Bharath B R, Manjunatha H, DPPH scavenging assay of novel 1,3-disubstituted-1H-pyrazol-5-ols and their in silico studies on some proteins involved in Alzheimer's disease signaling cascade. Letters in Drug Design & Discovery, 2011, 7, 214-224
13. Blois M S. Antioxidant determinations by the use of a stable free radical. Nature 1958; 26: 1199-1200
14. Nishikimi M, Appaji N, Yagi K, The occurrence of superoxide anion in the reaction of reduced phenazine methosulfate and molecular oxygen, Biochemical and Biophysical Research Communications, 1972, 46, 849-854
15. Oyaizu M, Studies on product of browning reaction prepared from glucose amine. Japan Journal of Nutrition, 1986, 44, 307-315
16. Prieto P, Pineda M and Aguilar M. Spectrophotometric quantitation of antioxidant capacity through the formation of a Phosphomolybdenum Complex: Specific application to the determination of vitamin E. Analytical Biochemistry, 1999, 269, 337-341.
17. Frayling T M, Timpson N J, Weedon M N, Zeggini E, Freathy R M, Lindgren C M, Perry J R, Elliott K S, Lango H, Rayner N W, Shields B, Harries L W, Barrett J C, Ellard S, Groves C J, Knight B, Patch A M, Ness A R, Ebrahim S, Lawlor D A, Ring S M, Ben-Shlomo Y, Jarvelin M R, Sovio U, Bennett A J, Melzer D, Ferrucci L, Loos R J, Barroso I, Wareham N J, Karpe F, Owen K R, Cardon L R, Walker M, Hitman G A, Palmer C N, Doney A S, Morris A D, Smith G D, Hattersley A T, McCarthy M I (2007). A common variant in the FTO gene is associated with body mass index and predisposes to childhood and adult obesity. *Science* 316 (5826): 889-94.
18. Melnikova I, Wages D (2006). Antiobesity therapies. *Nature Reviews Drug Discovery* 5, 369-370.
19. Rodriguez A, Infante D (2011). Characterization in silico of flavonoids biosynthesis in *Theobroma cacao* L. *Network Biology* 1: 34-45.
20. Shi Y, Burn P (2004). Lipid metabolic enzymes: emerging drug targets for the treatment of obesity. *Nature Reviews Drug Discovery* 3: 695-710.
21. Shoelson S E, Herrero L, Naaz A (2007). Obesity, inflammation and insulin resistance, *Gastroenterology* 132(6): 2169-80.
22. Strader C D, Hwa J J, Van Heek M, Parker E M (1998). Novel molecular targets for the treatment of obesity. *Drug Discovery Today* 3: 250-256.

We claim:
1. A composition comprising a mixture of chlorogenic acids, said mixture consisting of: 12.5% 3-caffeoylquinic acid (3-CQA), 46.9% 5-caffeoylquinic acid (5-CQA), 17.2% 4-caffeoylquinic acid (4-CQA), 4.6% 5-feruloylquinic acid (5-FQA), 6.2% 3,4 dicaffeoylquinic acid (3,4 di CQA), 4.6% 3,5 dicaffeoylquinic acid (3,5 di CQA), and 8.0% 4,5 dicaffeoylquinic acid (4,5 di CQA).
2. The composition of claim 1, wherein the composition is formulated as a powder, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol or injection.
3. The composition of claim 1, wherein said composition is obtained by a process comprising:

a) contacting green coffee beans with a first solvent under conditions sufficient to produce an extract comprising chlorogenic acids;
b) removing said first solvent from said extract to produce a concentrated extract comprising said chlorogenic acids;
c) dissolving said concentrated extract in a second solvent to produce a concentrated extract solution comprising said chlorogenic acids;
d) contacting said concentrated extract solution with a resin under conditions sufficient to collect said chlorogenic acids on said resin thereby separating said chlorogenic acids from said second solvent;
e) eluting said chlorogenic acids from said resin with a third solvent to produce an eluent comprising said third solvent and said chlorogenic acids; and
f) removing said third solvent from said eluent thereby producing said mixture of chlorogenic acids.

* * * * *